United States Patent [19]

Mehta

[11] Patent Number: 5,352,898
[45] Date of Patent: Oct. 4, 1994

[54] METHOD AND APPARATUS FOR PREPARING SLURRY SPECIMENS FOR CRYO-SCANNING ELECTRON MICROSCOPY

[75] Inventor: Sudhir Mehta, Plano, Tex.

[73] Assignee: Atlantic Richfield Company, Los Angeles, Calif.

[21] Appl. No.: 64,290

[22] Filed: May 18, 1993

[51] Int. Cl.[5] ............................................. H01J 37/18
[52] U.S. Cl. .................................. 250/443.1; 250/304; 250/307; 250/440.11; 250/442.11
[58] Field of Search ............. 250/443.1, 442.11, 440.1, 250/310, 306, 307, 304

[56] References Cited

U.S. PATENT DOCUMENTS

| | | | |
|---|---|---|---|
| 4,284,894 | 8/1981 | Sitte et al. | 250/443.1 |
| 5,043,144 | 8/1991 | Gordon et al. | 250/440.1 |

*Primary Examiner*—Paul M. Dzierzynski
*Assistant Examiner*—Kiet T. Nguyen
*Attorney, Agent, or Firm*—Michael E. Martin

[57] ABSTRACT

Cement slurries and similar compositions of matter may be examined by cryogenic scanning electron microscopy by preparing samples of slurries in small cylindrical specimen forming capsules which may be immersed in cryogenic fluid to freeze the cement slurries at different stages in hydration of the cement for analysis of the hydration process. The capsules are frangible so as to be able to easily remove the specimens after freezing whereupon the specimens are immersed in a cryogenic fluid and mounted in a specimen holder having cooperating support jaws which are operable from a point out of the cryogenic fluid to engage and retain the specimen on the holder. The holder is placed in a specimen preparation chamber which is maintained at a sufficiently low temperature and vacuum condition to minimize contamination of the specimen during preparation. The specimen preparation chamber is formed by a housing which includes a fracturing knife which is actuated after placement of the specimen in the chamber to fracture the specimen and expose an uncontaminated surface of the specimen for further preparation of the specimen for examination by scanning electron microscopy.

12 Claims, 2 Drawing Sheets

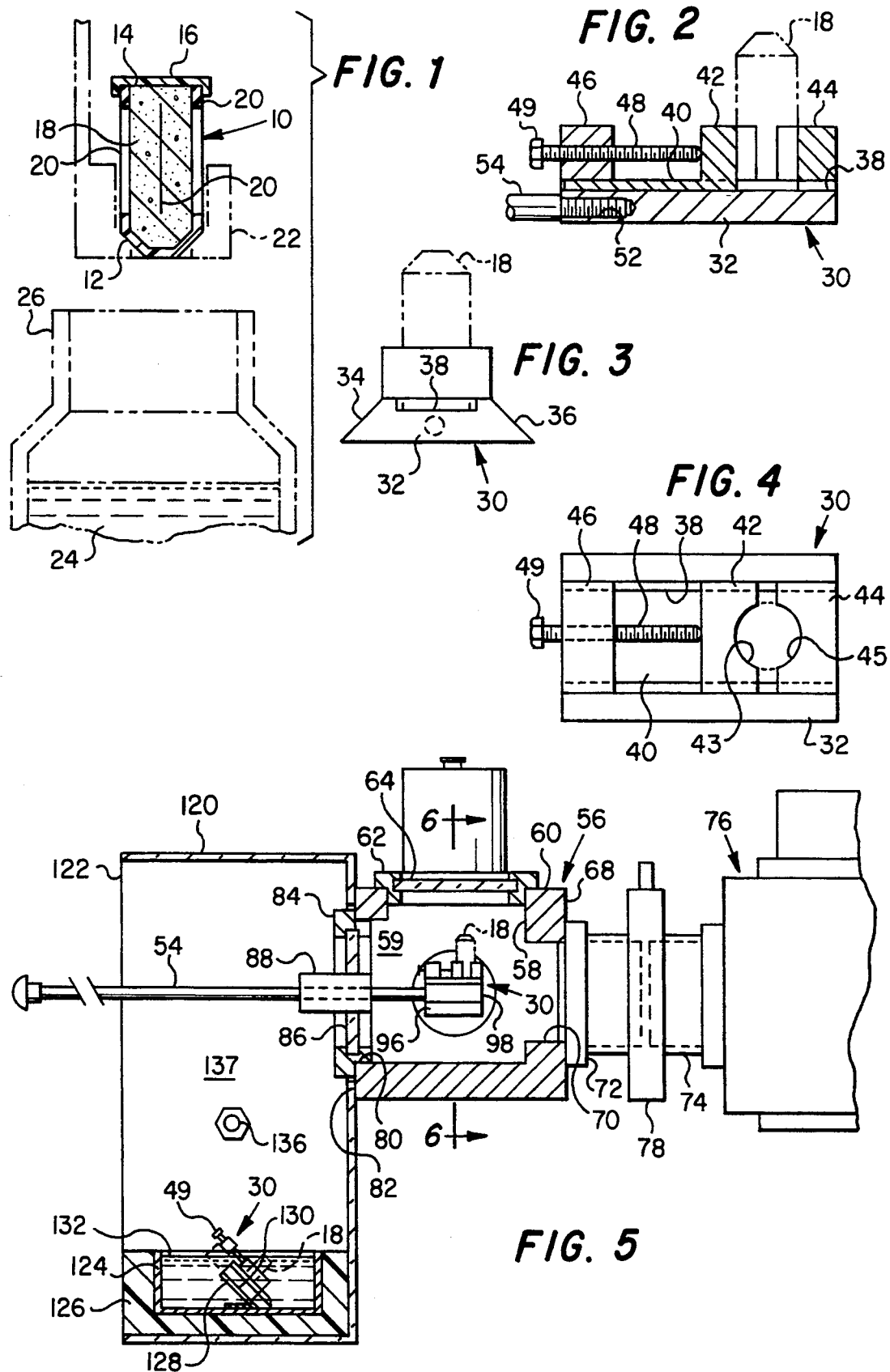

METHOD AND APPARATUS FOR PREPARING SLURRY SPECIMENS FOR CRYO-SCANNING ELECTRON MICROSCOPY

BACKGROUND OF THE INVENTION

1. Field of the Invention

The present invention pertains to a method and apparatus for preparing specimens comprising cement slurries and the like for microscopic analysis using cryogenic scanning electron microscopy.

2. Background

Certain compositions which pass from a liquid or slurried state to a solid state undergo complex reactions which are difficult to examine due to the changing properties of the composition between the slurried and the solid states. Certain cement materials, particularly those used in wellbore structures in the oil and gas industry, undergo hydration under difficult and widely varying conditions. Further knowledge about the cement hydration and "setting" process will provide a basis for improving cement formulas and preparing the wellbore for receiving cement compositions which will properly set and provide the desired properties upon setting.

Scanning electron microscopy (SEM), and particularly low-temperature or cryogenic scanning electron microscopy (CRYO-SEM), has become an important technique for assessing the nature of structural details of hydrated materials. The cryo SEM technique has also proven to be useful in locating and analyzing fluids within frozen samples and characterizing fast chemical reactions. However, the development of a procedure for analyzing frozen samples of certain slurried materials, such as cement slurries and slurries of certain waste materials which are to be disposed of in deep earth formations, must avoid contamination or unwanted changes in the properties of the samples or specimens during the preparation process. In particular, it has been considered desirable to be able to analyze the hydration of certain cement compositions at various times during the hydration process in order to better understand the process. A presentation entitled: "Cement Hydration During the First Twenty-Four Hours Examined By Cryo-Scanning Electron Microscopy" by Sudhir Mehta, et al and presented at the 15th International Conference on Cement Microscopy Mar. 28, 1993, discusses the results of CRYO-SEM analysis of certain oil well cements. However, a method of preparing specimens of such cements and similar materials for examination and certain apparatus used in the preparation, in accordance with the present invention, has been advantageous in assisting in the analysis of such specimens using CRYO-SEM.

SUMMARY OF THE INVENTION

The present invention provides an improved method for preparing specimens of certain materials including slurries of cement compositions and the like, for cryogenic scanning electron microscopy analysis.

In accordance with an important aspect of the present invention, an improved method of preparing specimens of cement slurries and similar slurried materials is carried out using a unique specimen holding capsule for freezing the specimen at a predetermined time and for removing the specimen from the capsule preparatory to further preparation and examination of the specimen.

In accordance with another important aspect of the present invention, a method is provided for preparing specimens for examination by cryogenic scanning electron microscopy (CRYO-SEM) wherein the specimen is prevented from exposure to atmospheric conditions which might damage or alter the physical or chemical properties of the specimen prior to final preparation and analysis by CRYO-SEM methodology. The specimens are substantially prevented from exposure to atmospheric air during a process of freezing the specimen and transferring the specimen to a unique specimen holder. The specimen is then further subjected to an improved preparation process by placement in a chamber which includes apparatus for fracturing the specimen to expose an uncontaminated surface on the specimen which is then suitable for application of a metallic coating thereto and placement in the scanning electron microscope.

The method and apparatus of the present invention provides for examining and isolating many of the reaction mechanisms which relate to the strength and stability of certain cement compositions and similar compositions of matter. In this way, certain reactions which take place over time when converting from a slurry form to a solid form may be modified and enhanced through a better understanding of the reaction characteristics. The effect of certain additives placed in the slurry such as retarders, dispersants, fluid loss additives, matrix intensifiers and strength enhancers may also be analyzed in an improved manner. In other words, by examining slurries such as cement slurries during the cement hydration process, the chemical or physical properties of the cement may then be more easily modified through the addition or deletion of certain elements in the composition. The improved method and apparatus also provides higher purity samples or specimens for SEM analysis than has heretofore been available.

The above-mentioned features and advantages of the present invention, together with other superior aspects thereof, will be further understood by those skilled in the art upon reading the detailed description which follows in conjunction with the drawing.

BRIEF DESCRIPTION OF THE DRAWING

FIG. 1 is a vertical central section view of a unique specimen preparation capsule in accordance with the present invention being prepared for freezing of a specimen of cement slurry or the like;

FIG. 2 is a side elevation, in section, of a unique specimen holder in accordance with the present invention;

FIG. 3 is an end view of the specimen holder;

FIG. 4 is a top plan view of the specimen holder;

FIG. 5 is a side elevation, in section, of an improved specimen preparation housing and an associated preparation enclosure in accordance with the present invention;

DESCRIPTION OF PREFERRED EMBODIMENTS

Figure 6:
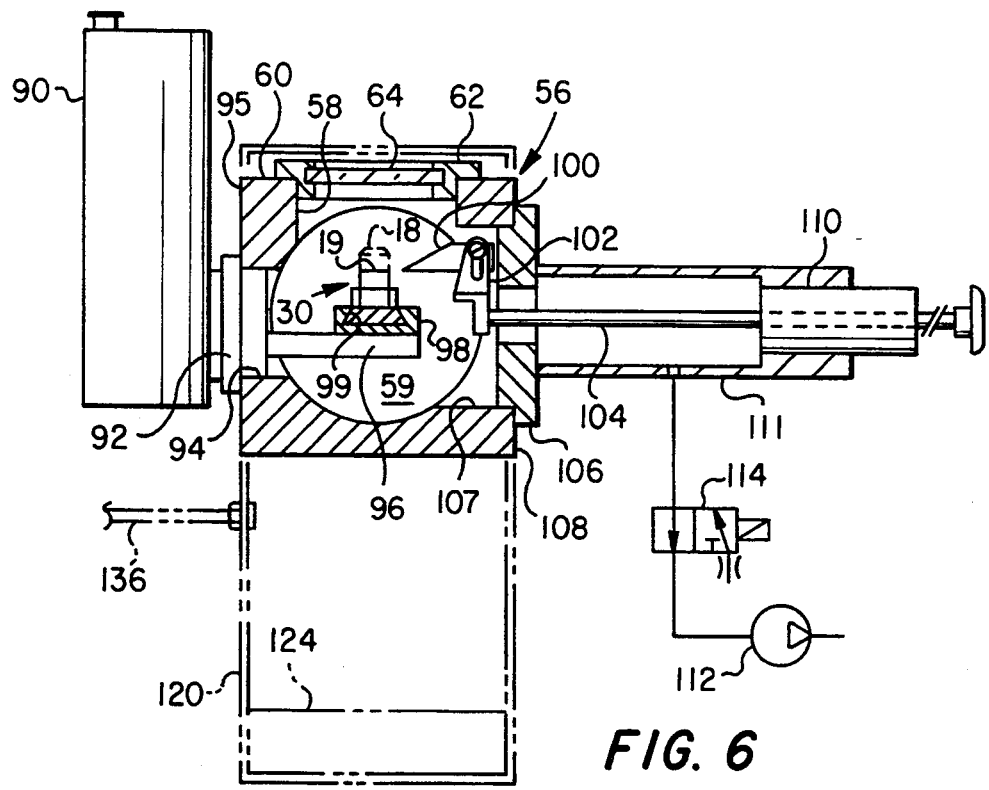
FIG. 6 is a section view taken substantially along the line 6—6 of FIG. 5.

In the description which follows, like parts are marked throughout the specification and drawing with the same reference numerals, respectively. The drawing figures are not necessarily to scale and are in somewhat schematic form in the interest of clarity and conciseness.

Referring to FIG. 1, there is illustrated a unique specimen preparation capsule in accordance with the present invention and generally designated by the numeral 10. The specimen capsule 10 comprises a generally cylindrical container having a frustoconical bottom part 12 and an upper, open end 14 which is shown temporarily closed by a suitable closure cap 16. The capsule 10 is preferably formed of high-density polypropylene or the like and is prepared for receiving a quantity of a slurry 18 to be frozen at a predetermined time, by forming a plurality of longitudinally extending slits 20, preferably either two or four in total number and spaced evenly apart about the circumference of the capsule. The slits 20 are formed by a very sharp knife or razor cut so as to remove as little material as possible and thereby prevent substantial leakage of slurry through the slits prior to introduction of the capsule into a cryogenic fluid. If slurries are of a low enough viscosity which might result in leakage through the slits 20, the exterior surface of the capsule 10 may be wrapped with a suitable tape, not shown.

In preparing the slurry specimen 18 for examination the slurry is allowed, in the case of cement materials or mixtures, to hydrate for a predetermined period of time after which the capsule 10 is disposed in a suitable holder 22 and then lowered into a quantity of cryogenic fluid such as liquid nitrogen 24 disposed in a suitable flask 26. For example, if a typical oil well cement, such as a class H cement, is to be examined at various stages of hydration, say after ten, thirty and sixty minutes of hydration, plural capsules 10 filled with a quantity of such slurry are, at the termination of the desired hydration periods, frozen in the cryogenic fluid 24 by lowering a capsule thereinto. In preparing specimens of oil well cement, for example, it is desirable to freeze the specimens 18 at −210° C. and not warmer than about −196° C., the boiling temperature of Nitrogen at nominal atmospheric conditions. After freezing a specimen 18 in the capsule 10, the capsule is withdrawn quickly from the cryogenic fluid, the cap 16 removed and the slits 20 extended by a knife or razor to the open end 14. A suitable blade is then inserted in the slits to break the wall segments of the capsule 10 away from the specimen 18 to allow it to be easily removed from the capsule. Removal of the specimen 18 from the capsule 20 and temporary storage of the specimen is preferably carried out in accordance with the method and further apparatus to be described hereinbelow.

In preparing the specimen 18 for examination by a scanning electron microscope a unique specimen holder has been developed in accordance with the present invention. Referring to FIGS. 2, 3 and 4, a specimen holder is illustrated and generally designated by the numeral 30. The holder 30 includes a base member 32 having inclined sides 34 and 36 to enable the holder to be suitably mounted in a "dovetail" slot of one or more support members to be described further herein. The base member 32 also has a longitudinally-extending, generally rectangular recess 38 formed therein for receiving a support key 40 of a specimen clamping jaw 42 slidably disposed on the base member 32. A second, stationary clamping jaw 44 is supported on the base member 32, as illustrated. The support key 40 is slidably retained in the slot 38 by a stationary support member 46 disposed on the base member 32 and adapted to support a clamping jaw retaining screw 48 threadedly engaged therewith. The retaining screw 48 includes a drive head 49 and the screw is suitably engaged with the specimen clamping jaw 42, as illustrated in FIGS. 2 and 4. The jaws 42 and 44 each have suitable arcuate recesses 43 and 45 formed therein, see FIG. 4, for engagement with a specimen 18 and for forcibly clamping the specimen on the holder 30. The holder 30 is also provided with a suitable threaded recess 52, FIG. 2, in one end of the base member 32 for receiving the threaded distal end of a positioning rod 54, the purpose of which will be explained in further detail herein.

Referring now to FIGS. 5 and 6, there is illustrated an improved specimen preparation housing for use with a cryogenic scanning electron microscope in accordance with the method of the present invention. The specimen preparation housing is generally designated by the numeral 56 and is of a general type commercially available and modified by the University of Minnesota in certain respects which are not part of the present invention. The housing 56 comprises a somewhat rectangular block-shaped member having a generally cylindrical opening 58 formed in a top wall 60. The opening 58 is closed by a removable cover 62 having a viewing window 64 formed therein. The cover 62 is preferably secured to the housing 56 by suitable fasteners, not shown. One sidewall 68 of the housing 56 includes a cylindrical opening 70 formed therein for receiving a flanged cover portion 72 of a conduit 74 which is adapted to connect the housing 56 to a metallic coating application housing, generally designated by the numeral 76, and having a closable coating application chamber 79 formed thereby. The metallic coating application housing 76 may be of a type commercially available and suitable for applying a very thin metallic coating to the surface of specimens to be examined by a scanning electron microscope. A suitable gate valve 78 is interposed in the conduit 74 to isolate the interior of the metallic coating housing 76 from a chamber 59 formed within the housing 56, which chamber is substantially formed by the intersection of the bores or openings 58, 70 and a cylindrical opening 80 formed in a sidewall 82 of the housing 56 opposite the sidewall 68. The opening 80 is closed by a removable cylindrical cover 84 having a suitable window 86 formed therein and also supporting a bearing and seal assembly 88 for the positioning rod 54. The rod 54 is slidable in the bearing and seal assembly 88 while preventing communication of fluid into the space 59. The cover 84 is adapted to be snuggly fitted in the bore or opening 80 and held firmly therein in fluid tight engagement with the housing 56 by differential pressure when the space 59 is under vacuum conditions.

Referring also to FIG. 6, the specimen preparation housing 56 further includes a source of cryogenic fluid such as liquid nitrogen comprising a flask 90 which is supported on a removable cover 92 disposed in a cylindrical bore or opening 94 formed in a third sidewall 95 of the housing 56. A support member 96 projects from the cover 92 into the space 59 and supports a further support member 98 having a dovetail slot 99 formed therein for receiving the sample holder 30, as shown. Cryogenic fluid such as liquid nitrogen contained in the flask 90 will be in heat exchange relationship with the cover 92 and the support 96 to effect maintenance of the space 59 at a temperature which will prevent thawing of the specimen 18.

The specimen 18 is prepared for application of a metallic coating and eventual scanning electron microscopy by exposing an uncontaminated examination surface 19 on the specimen, see FIG. 6. The surface 19 is exposed by fracturing the specimen 18 to remove that portion of the specimen above the surface 19, viewing FIG. 6, by an impact knife or chisel member 100 disposed in the space 59 and supported on a support member 102 which is connected to an actuating rod 104. The actuating rod 104 is supported in the position shown by a removable flanged cover member 106 which is suitably supported on the housing 56 in a cylindrical opening 107 formed in a sidewall 108 opposite the sidewall 95. The knife actuating rod 104 extends through and is supported on a bearing and seal assembly 110 which is supported by a tubular housing member 111 secured to the cover 106.

As shown in FIG. 6, the space 59 may be maintained at a relatively high vacuum by a vacuum pump 112 which is in communication with the space 59 by way of the housing 111 and a suitable control valve 114. The valve 114 is operable in one position to place the chamber 59 in communication with the vacuum pump 112 to maintain a predetermined vacuum condition in the space through suitable control means, not shown. In a second position of the valve 114, the space 59 is placed in communication with atmospheric conditions around the housing 56 to substantially equalize the pressure between the space 59 and the exterior of the housing so that the cover 84, together with the positioning rod 54 and the specimen holder 30 may be removed from the housing 56 to replace the specimen 18 with another specimen, for example.

Referring again to FIG. 5, the sample preparation apparatus further includes a transparent enclosure 120 supported on the housing 56 against the sidewall 82 and having one open side 122, as indicated. The enclosure 120 is operable to receive a sample preparation container 124 having a suitable exterior insulating receptacle 126. The container 124 includes a holder support member 128 having a suitable dovetail slot 130 formed therein for receiving the specimen holder 30 in supporting relationship thereto and submerged in a bath of liquid nitrogen or other suitable cryogenic fluid 132. The enclosure 120 may also be connected to a source of cryogenic fluid such as liquid nitrogen by way of a conduit 136 whereby the space 137 within the enclosure may be maintained full of an inert gas at a temperature below the ambient temperature of the atmosphere in which the apparatus is situated to minimize intrusion and condensation of atmospheric water vapor during placing of a specimen into the holder 30 and placing the holder 30 in the space 59.

A method for preparing a sample of partially hydrated cement for analysis by a CRYO-SEM method will now be described. A sample 18 is prepared by placing a quantity of cement slurry of known composition in a capsule 10 which has been slit to provide the slits 20, as illustrated in FIG. 1. The removable cap 16 is placed over the open end 14 of the capsule to prevent loss of specimen material. The capsule 10 is then placed in the holder 22 and lowered into cryogenic fluid such as liquid nitrogen at a temperature as low as $-210°$ C. and allowed to remain in the fluid until the specimen is frozen. The age of the specimen 18 may be predetermined so that the degree of hydration or other reaction taking place in the specimen can be observed by the scanning electron microscope. When the specimen 18 is suitably frozen, it is removed from the cryogenic fluid 24, the cap 16 is removed from the capsule 10 and the specimen 18 is removed from the capsule by cutting the slits 20 to the open end 14 and prying the segments of the capsule between the slits apart to allow the specimen to be removed from the capsule. The process of removing the specimen 18 from the capsule 10 may be carried out within the space 137 of the enclosure 120 and directly over the container 124 so that the frozen specimen 18 may be placed immediately into the cryogenic fluid 132 in the container.

A holder 30 has, preferably, been prepositioned in the temporary support 128 substantially submerged in the cryogenic fluid 132 in the container 124. A suitable tool, such as a pair of tweezers or the like, may be utilized to manipulate the specimen 18 to place it between the jaws 42 and 44 of the holder 30 without removing it from the fluid 132. Then the specimen 18 in the holder may be secured by adjusting the position of the retaining screw 48 to tightly clamp the specimen between the jaws 42 and 44. The holder 30 may or may not be disconnected from the positioning rod 54 during the process of loading a specimen 18 into the holder. As will be appreciated from the foregoing description, a minimum amount of exposure of the specimen 18 to atmospheric pressure, temperature and humidity conditions is experienced during the placement of the specimen in the holder 30. When the specimen 18 is disposed in the holder 30, it is substantially submerged in the cryogenic fluid 132 in the preparation container 124.

The positioning rod 54 is then threaded into the recess 52 in the holder 30. Prior to this operation, the space 59 of the housing 56 has been brought to atmospheric pressure by moving the valve 114 to allow the pressure in the space 59 to equalize with atmospheric pressure. This will allow removal of the rod 54 in assembly with the cover 84 from the housing 56 since the cover 84 is normally retained in sealing engagement with the housing by the pressure differential between the space 59 and the exterior of the housing. Moreover, prior to allowing the pressure in the space 59 to reach ambient atmospheric pressure, the valve 78 is normally closed so that the interior of the metal coating application housing 76 and the interior of the scanning electron microscope are maintained at a suitable vacuum and temperature condition.

The positioning rod 54, in assembly with the cover 84, is connected to the holder 30 and the holder is then quickly placed in the space 59, the cover 84 centered in the opening 80 and the rod 54 moved to place the holder 30 in slot 99 of the support 98. The valve 14 may have already been moved to the position to place the space 59 in communication with the vacuum pump 112 so that once the cover 84 is positioned in the opening 80, a rapid decrease in pressure in the space 59 will occur to secure the cover in the position shown in FIG. 5. The support 98, together with its support arm 96 and the housing 56, are maintained at a suitably low temperature thanks to the conductive heat exchange between these parts and the cryogenic fluid disposed in the flask 90 supported on the housing 56. Once the specimen 18 is placed in the position shown in FIGS. 5 and 6 and the pressure and temperature in the space 59 brought to a suitable condition as determined by suitable pressure and temperature measuring instruments, not shown, a substantially uncontaminated surface of the specimen 18, such as the surface 19, FIG. 6, is prepared by fracturing or cutting the specimen 18 with the impact knife 100. Upon placing the specimen 18 into the space 59 the knife 100 is placed in a retracted position, as shown in FIG. 6, by pulling the actuating rod 104 to the right, viewing FIG. 6.

Figure 7:
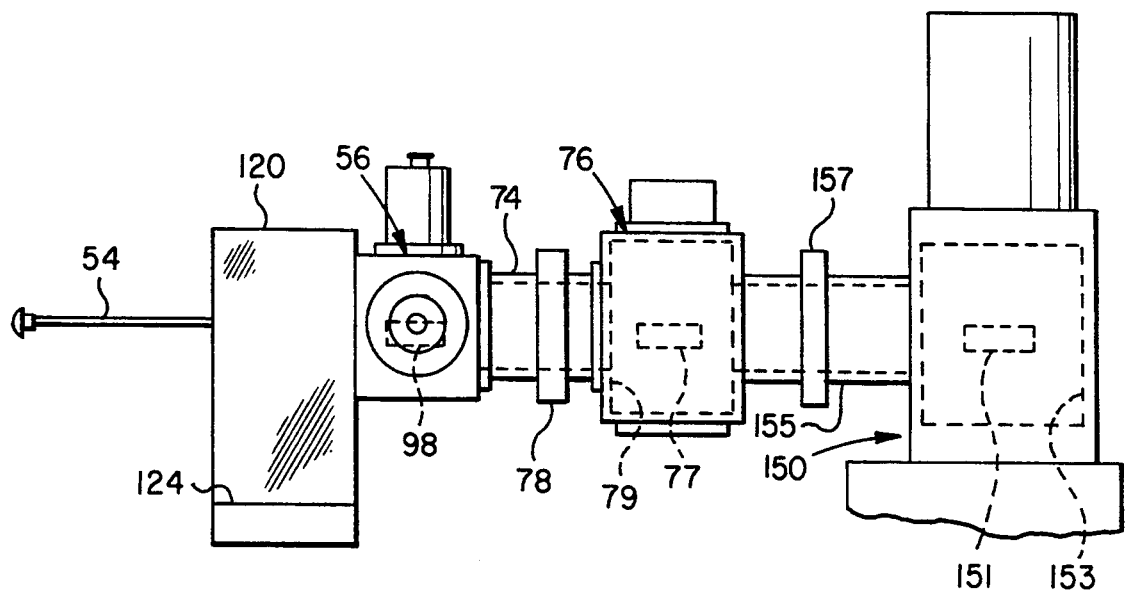
FIG. 7 is a side view showing the arrangement of the specimen preparation housing in relation to the metallic coating chamber and the examination chamber of a scanning electron microscope.

Once the specimen 18 is suitably secured on the support 98, the rod 104 may be moved rapidly to the left, causing the knife or chisel 100 to impact the specimen 18 and shear off the top portion of the specimen leaving the surface 19 exposed to the conditions in the space 59, which conditions are essentially the same as the conditions to which the specimen will be exposed during application of a metal coating and eventual observation by the scanning electron microscope. After fracturing the specimen 18 with the knife 100 to expose the surface 19, the specimen is ready for application of a suitable metallic coating to enhance the scanning electron microscopy. FIG. 7 shows the general arrangement of the housing 56, the metallic coating application housing 76 and a suitable scanning electron microscope, generally designated by the numeral 150. The microscope may be of a type commercially available such as an ISI Model WB6, distributed by Topcon Technology, Inc. of Pleasanton, Calif. The metallic coating application housing 76 may also be of a type commercially available and used by others such as by the University of Minnesota CRYO-SEM Laboratory.

Both the housing 76 and the scanning electron microscope 156 include suitable support stages 77 and 151 similar to the support member 98 for receiving and supporting the holder 30 in a suitable dovetail slot formed in each of these support stages. The support stage 151 is disposed in a suitable examination chamber 153 formed in the scanning electron microscope 150 and which is in communication with the chamber 79 of the housing 76 by way of a suitable conduit 155 having a shut-off valve 157 interposed therein. Accordingly, the chamber 79 and the chamber 153 are maintained at a suitable vacuum and temperature condition by equipment similar to the pump 112 and the source of cryogenic fluid 90 so that conditions of applying a metal coating to the specimen and performing scanning electron microscopy will be carried out without altering the characteristics of the specimen.

When the specimen 18 has been prepared for application of a metal coating, the rod 54 is manipulated to remove the holder 30 from the support member 98 and position the holder on the support stage 77 preparatory to applying a metallic coating to the surface 19. After application of the above-mentioned coating to the specimen, the holder 30 is then further manipulated by the rod 54 to position it on the support stage 151 of the microscope 150 whereby suitable microscopic examination may be carried out. The specimen 18 may be withdrawn from the microscope and the housing 76 by manipulation of the rod 54 to place the specimen back in the space 59 and closure of the valve 78. After positioning the valve 114 to allow pressure in the space 59 to substantially equalize with that of the atmospheric conditions outside the housing 56 the cover 84, in assembly with the rod 54 and the holder 30, are removed from the housing 56 and the enclosure 120. The holder 30 is then disconnected from the rod 54 and replaced with another holder already in the support 128 preparatory to placing another specimen in the space 59 for preparation to receive the metallic coating aforementioned and to be microscopically examined.

The method of the present invention may be carried out with a capsule capable of producing specimens of about 0.25 inches diameter frozen at or colder than $-210°$ C. The temperature in the chamber 59 is preferably maintained at or colder than $-160°$ C. and the process of placing the specimen 18 in the chamber is carried out without significant exposure of the specimen to room temperature, pressure and humidity conditions. The vacuum in the space 59 is preferably maintained at or lower than about $2 \times 10^{-5}$ torr so that uncontaminated surfaces of the specimens may be exposed for examination. After fracturing a specimen 18 to expose a surface 19, for example, the specimen is transferred into the metal coating housing 76 and coated with a conductive film of chromium of a thickness of about 100 angstroms, for example. The coated specimens are then transferred into the scanning electron microscope wherein the temperature and pressure conditions are maintained essentially at those in the space 59. As pointed out in the abovementioned publication, the CRYO-SEM characterization of cement specimens frozen after ten, thirty, and sixty minutes and 24 hours of hydration have revealed several interesting characteristics of the hydration rate of class H type cement, for example. Moreover, the results of the method and use of the apparatus of the present invention described herein illustrate that the cryogenic scanning electron microscope methodology is a viable technique in analyzing the complexities of cement hydration as well as the reactions that take place with many types of slurried solids materials which undergo chemical and physical changes after formation of the slurry.

Although preferred embodiments of the present invention have been described in detail herein, those skilled in the art will recognize that various substitutions and modifications may be made to the specific method and apparatus described without departing from the scope and spirit of the invention as recited in the appended claims.

What is claimed is:

1. A method for preparing a specimen comprising, at room temperature, one of a slurry and viscous liquid, for examination by a scanning electron microscope comprising the steps of:

placing a specimen of said slurry in a capsule and freezing said specimen;

removing said frozen specimen from said capsule and transferring said frozen specimen to a specimen holder without exposing said specimen to room temperature, atmospheric pressure and humidity conditions for a substantial period of time;

placing said specimen and said holder in a space exposed to a temperature not greater than about $-160°$ C. and at a pressure less than atmospheric pressure; and fracturing said specimen to expose an uncontaminated surface of said specimen which has not been exposed to said room temperature, atmospheric pressure and humidity conditions.

2. The method set forth in claim 1 wherein:

said capsule comprises a cylindrical member having a plurality of longitudinal slits formed therein and the step of removing said specimen from said capsule comprises the step of prying walls of said capsule away from each other at said slits to free said specimen from said capsule.

3. The method set forth in claim 1 wherein:

said specimen is frozen by placing said capsule containing said specimen in a cryogenic fluid at a temperature of not more than $-196°$ C.

4. The method set forth in claim 1 wherein:
the step of transferring said specimen to said holder includes the step of placing said specimen in said holder while exposed to a cryogenic fluid.

5. The method set forth in claim 4 wherein:
said specimen is transferred from said capsule to said holder by disposing said holder in a container having a quantity of said cryogenic fluid therein and substantially covering said holder, and said specimen is removed from said capsule and placed in said container and then in said holder to substantially obviate exposure of said specimen to said atmospheric pressure, room temperature and humidity conditions.

6. The method set forth in claim 5 further including the steps of:
removing said holder from said container while exposed to an inert vapor, placing said holder on a support member disposed in said chamber and exposing a quantity of cryogenic fluid through said support member to reduce and maintain the temperature of said holder disposed in said chamber.

7. A method of preparing specimens of cement compositions for cryogenic scanning electron microscopy analysis of the hydration characteristics of said cement compositions, comprising the steps of:
preparing a specimen of a cement slurry and placing a quantity of said slurry in a specimen support capsule;
allowing said specimen of said cement slurry in said capsule to hydrate for a predetermined period of time;
after said predetermined period of time, immersing said capsule containing said specimen in a cryogenic fluid to freeze said specimen at a temperature less than about $-196°$ C. to arrest said hydration of said cement composition;
transferring said specimen from said capsule to a holder without exposing said specimen to atmospheric pressure, room temperature and humidity conditions;
placing said holder containing said specimen on a support member disposed in a housing which is evacuated and frozen to prevent thawing of said specimen; and
fracturing said specimen to expose an uncontaminated surface of said specimen for examination by a scanning electron microscope.

8. A specimen holder for use in preparing and supporting a specimen of frozen composition of matter for examination by a scanning electron microscope having a support stage, said specimen holder comprising:
a base member including surfaces formed thereon and cooperate with guide surfaces formed on a holder support member, said holder support member disposed in a preparation chamber, a fixed specimen support jaw on said base member, a movable specimen support jaw disposed on said base member and cooperated with said fixed support jaw to grip and support said a specimen for fracturing of said specimen and for subsequent examination of said specimen, a retaining member engaged with said movable jaw for exerting a clamping force on said movable jaw to clamp said specimen between said jaws of said specimen holder; and
means for connecting said specimen holder to a positioning rod for moving said specimen holder into said holder support member in said specimen preparation chamber and into said support stage in said scanning electron microscope.

9. The specimen holder set forth in claim 8 wherein:
said retaining member includes a head engaged by tool means for moving said retaining member to engage said movable jaw, said head is disposed at one end of said specimen holder and said means for connecting said specimen holder to said positioning rod is disposed at said one end of said specimen holder.

10. The specimen holder set forth in claim 8 further in combination with:
a support member for said specimen holder disposed in a container having a quantity of cryogenic fluid disposed therein and wherein said specimen holder projects generally upwardly out of said container and said cryogenic fluid for operating said specimen without entering said retaining member and said means for connecting said specimen holder to said positioning rod.

11. A specimen preparation housing for use in conjunction with a scanning electron microscope for cryogenic scanning electron microscopy of specimens of frozen slurries of compositions of matter, said specimen preparation housing defining a closable chamber for receiving a specimen, and said housing including:
a specimen holder for holding a specimen;
a support member having guide surfaces formed thereon and cooperated with surfaces formed on said specimen holder for supporting said specimen holder, said support member disposed in said chamber and connected to a source of refrigeration outside said chamber to reduce and maintain the temperature of said specimen holder and said specimen during presence of said specimen in said chamber;
means for inserting said specimen holder and said specimen into said support member in said chamber; and
means for fracturing said specimen in said chamber including an actuating rod for effecting actuation of said means for fracturing upon placement of said specimen in said chamber to expose an uncontaminated surface of said specimen after placement of said specimen in said chamber.

12. The specimen preparation housing set forth in claim 11 wherein:
said means for fracturing comprises a knife member connected to said actuating rod and responsive to movement of said actuating rod to engage and fracture said specimen to expose uncontaminated surface.

* * * * *